United States Patent [19]

Goldmann et al.

[11] Patent Number: 4,668,691

[45] Date of Patent: May 26, 1987

[54] CIRCULATION-ACTIVE NOVEL 7-ARYL-OR PYRIDYL-1-OXO-1,C,4,7-TETRAHYDROBENZOFURANS

[75] Inventors: Siegfried Goldmann, Wuppertal; Matthias Schramm, Cologne; Günter Thomas; Rainer Gross, both of Wuppertal, all of Fed. Rep. of Germany

[73] Assignee: Bayer Aktiengesellschaft, Leverkusen, Fed. Rep. of Germany

[21] Appl. No.: 724,374

[22] Filed: Apr. 18, 1985

[30] Foreign Application Priority Data

May 3, 1984 [DE] Fed. Rep. of Germany ....... 3416293

[51] Int. Cl.$^4$ .................... C07D 407/02; A61K 31/44
[52] U.S. Cl. .................................... 514/337; 514/469; 514/432; 514/333; 546/269; 546/274; 546/256; 549/302; 549/23; 549/59; 549/60; 548/564; 548/336
[58] Field of Search ................ 514/469, 337; 549/302; 546/269, 256, 333

[56] References Cited

U.S. PATENT DOCUMENTS 4,491,667 1/1985 Saitu et al. .......................... 549/302

Primary Examiner—Jane T. Fan
Attorney, Agent, or Firm—Sprung Horn Kramer & Woods

[57] ABSTRACT

1-Oxo-1,3,4,7-tetrahydrobenzofuranes of the formula

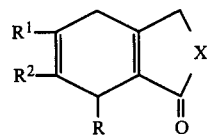

in which
X is O or S,
R is optionally substituted phenyl or heteroaryl,
$R^1$ is OH, monoalkylamino or dialkylamino, and
$R^2$ is an acyl or esterified carboxy radical, or pharmacologically acceptable salts thereof, which are active in circulation, e.g. they increase myocardial contractility, increase the flow of $Ca^{2+}$ into the cell, increase blood pressure, reduce blood sugar, reduce swelling of mucous membranes and affect the salt and/or fluid balance.

11 Claims, No Drawings

CIRCULATION-ACTIVE NOVEL 7-ARYL-OR PYRIDYL-1-OXO-1,C,4,7-TETRAHYDROBENZOFURANS

The present invention relates to new fused furanones, to several processes for their preparation, and to their use in medicaments, in particular in medicaments affecting the circulation.

The new furanones are characterized by the following general formula (I)

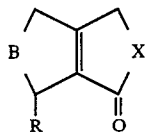

in which
R represents a phenyl, naphthyl, thienyl, furyl, pyrryl, pyrazolyl, imidazolyl, oxazolyl, isoxazolyl, thiazolyl, pyridyl, pyridazinyl, pyrimidyl, pyrazinyl, quinolyl, isoquinolyl, indolyl, benzimidazolyl, quinazolyl, quinoxalyl, thionaphthenyl, isothionaphthenyl, chromonyl, thiochromonyl, chromenyl, thiochromenyl, benzoxadiazolyl or benzothiadiazolyl radical, it being possible for the radicals mentioned optionally to contain 1 to 3 identical or different substituents from the group comprising alkyl (1 to 20 carbon atoms), alkenyl (2 to 20 carbon atoms), alkinyl (2 to 20 C atoms), alkoxy (1 to 20 C atoms), fluorine, chlorine, bromine, iodine, trifluoromethyl, monofluoroalkoxy (1 to 10 C atoms), polyfluoroalkoxy (1 to 10 C atoms), hydroxyl, amino, monoalkylamino (1 to 10 C atoms), dialkylamino (1 to 10 C atoms), nitro, cyano, azido, carboxyl, carbalkoxy ($C_1$-$C_{10}$), carboxamido, sulphonamido, $SO_m$-alkyl (m=0 to 2, 1 to 20 C atoms), phenyl, benzyl, benzyloxy or benzylthio, it being possible in turn for the 4 last-mentioned substituents optionally to contain 1 to 3 radicals from the group comprising alkyl (1 to 5 C atoms), alkoxy (1 to 5 C atoms), alkylthio (1 to 5 C atoms), fluorine, chlorine, bromine, iodine, cyano, nitro, azido, hydroxyl, trifluoromethyl, amino, alkylamino (1 to 6 C atoms) or dialkylamino (1 to 6 C atoms), B represents the group

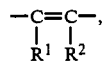

it being necessary for $R^2$ and R to be located on adjacent carbon atoms,
$R^1$ represents hydroxyl, NH-alkyl (1 to 15 C atoms) or N(alkyl)$_2$ (each 1 to 15 C atoms), and
$R^2$ represents the radical —COR$^3$ or COOR$^3$,
where
$R^3$ denotes a straight-chain, branched or cyclic, saturated or unsaturated hydrocarbon radical having 1 to 20 C atoms, which is optionally substituted by alkoxy having 1 to 10 C atoms, alkylthio having 1 to 10 C atoms, alkylsulphinyl having 1 to 10 C atoms, trialkylsilyl having 1 to 6 C atoms in each case, halogen, cyano, hydroxyl, amino, alkylamino having 1 to 6 C atoms, dialkylamino having 1 to 6 C atoms in each case, morpholinyl, piperidyl, piperazinyl, nitro, nitrate, aryl or heteroaryl, which can optionally be substituted by 1 to 3 identical or different substituents from the group comprising halogen, alkyl having 1 to 6 C atoms, alkoxy having 1 to 6 C atoms, alkylthio having 1 to 6 C atoms, alkylsulphinyl having 1 to 6 C atoms, alkylsulphonyl having 1 to 6 C atoms, hydroxyl, cyano, nitro, amino, alkylamino having 1 to 6 C atoms, dialkylamino having 1 to 6 C atoms in each case, monofluoroalkyl or polyfluoroalkyl having 1 to 6 C atoms, or monofluoroalkoxy or polyfluoroalkoxy having 1 to 6 C atoms, and
X represents O or S,
and their physiologically acceptable salts.

Preferred compounds of the general formula I which may be mentioned are those
in which
R represents a phenyl, naphthyl, thienyl, pyrazolyl, imidazolyl, isoxazolyl, thiazolyl, pyridyl, pyridazinyl, pyrimidyl, pyrazinyl, quinolyl, isoquinolyl, indolyl, benzimidazolyl, quinazolyl, quinoxalyl, thionaphthenyl, isothionaphthenyl, chromonyl, thiochromonyl, chromenyl, thiochromenyl, benzoxadiazolyl or benzothiadiazolyl radical, it being possible for the radicals mentioned optionally to contain 1 to 3 identical or different substituents from the group comprising alkyl (1 to 20 carbon atoms), alkenyl (2 to 16 carbon atoms), alkinyl (2 to 16 C atoms), alkoxy (1 to 16 C atoms), fluorine, chlorine, bromine, iodine, trifluoromethyl, monofluoroalkoxy (1 to 8 C atoms), polyfluoroalkoxy (1 to 8 C atoms), hydroxyl, amino, monoalkylamino (1 to 8 C atoms), dialkylamino (1 to 8 C atoms), nitro, cyano, azido, carboxyl, carbalkoxy ($C_1$-$C_8$), $SO_m$-alkyl (m=0 to 2, 1 to 14 C atoms), phenyl, benzyl, benzyloxy or benzylthio, it being possible for the 4 last-mentioned substituents optionally to contain 1 to 3 radicals from the group comprising alkyl (1 to 3 C atoms), alkoxy (1 to 3 C atoms), alkylthio (1 to 3 C atoms), fluorine, chlorine, bromine, iodine, cyano, nitro, hydroxyl, trifluoromethyl, amino, alkylamino (1 to 3 C atoms) or dialkylamino (1 to 3 C atoms), B represents the group

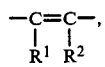

it being necessary for $R^2$ and R to be located on adjacent carbon atoms,
$R^1$ represents hydroxyl, NH-alkyl (1 to 10 C atoms) or N(alkyl)$_2$ (each 1 to 10 C atoms), and
$R^2$ represents the radical COOR$^3$,
where
$R^3$ represents a straight-chain, branched or cyclic, saturated or unsaturated hydrocarbon radical having up to 14 C atoms, which is optionally substituted by alkoxy having 1 to 6 C atoms, alkylthio having 1 to 6 C atoms, alkylsulphinyl having 1 to 6 C atoms, trialkylsilyl having 1 to 4 C atoms in each case, halogen, cyano, hydroxyl, amino, alkylamino having 1 to 4 C atoms, dialkylamino having 1 to 6 C atoms in each case, piperidyl, nitro, nitrate, phenyl or pyridyl, which can optionally be substituted by 1 to 3 identical or different substituents from the group comprising halogen, alkyl having 1 to 4 C atoms, alkoxy having 1 to 4 C atoms, alkylthio having 1 to 4 C atoms, alkylsulphinyl having 1 to 4 C atoms, alkylsulphonyl having 1 to 4 C atoms, hydroxyl, cyano, nitro, amino, alkylamino having 1 to 4 C atoms, dialkylamino having 1 to 4 C atoms in each case, monofluoroalkyl or polyfluoroalkyl having 1 to 4 C atoms, or monofluoroalkoxy or polyfluoroalkoxy having 1 to 4 C atoms, and X represents O or S.

Particular interest attaches to compounds of the general formula I
in which
R represents phenyl, naphthyl, pyridyl or thiochromenyl, it being possible for the phenyl radical optionally to be substituted 1 to 3 identical or different substituents from the group comprising alkyl having 1 to 4 carbon atoms, fluorine, chlorine, nitro, trifluoromethyl, alkoxy having 1 to 4 carbon atoms, hydroxyl, amino, dialkylamino having 1 to 4 C atoms in each case, cyano, carboxyl, carbalkoxy, phenyl, benzyl, benzyloxy or benzylthio, the 4 last-mentioned substituents in turn optionally bearing 1 or 2 identical or different substituents from the group comprising alkyl, alkoxy, alkylthio having 1 to 4 C atoms in each case, fluorine, chlorine, cyano, hydroxyl, trifluoromethyl or nitro,
B represents the group $$-\underset{\underset{R^1}{|}}{C}=\underset{\underset{R^2}{|}}{C}-,$$

it being necessary for $R^2$ and R to be located on adjacent carbon atoms,
$R^1$ represents hydroxyl, NH-alkyl having 1 to 4 C atoms or dialkylamine having 1 to 4 C atoms in each alkyl group, and
$R^2$ represents the radical $COOR^3$,
where
$R^3$ represents a straight-chain, branched or cyclic alkyl or alkenyl radical having up to 12 C atoms which is optionally substituted by alkoxy or alkylthio having 1 to 4 C atoms in each case, fluorine, chlorine, cyano, hydroxyl, amino, alkylamino or dialkylamino having 1 to 4 C atoms in each alkyl group, nitro, phenyl or pyridyl, and
X represents oxygen.

The compounds of the general formula (I) in which $R^1 \neq OH$, can be prepared by
(A) reacting aldehydes of the general formula (II)

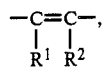  (II)

in which R has the abovementioned meaning, with compounds of the general formula (III)

$$HC(R_2)=C(R_1)-CH_3 \qquad (III)$$

in which $R_1$ and $R_2$ have the abovementioned meanings, and compounds of the general formula (IV)

$$R^4-OOC-CH_2-CO-CH_2-X-R^5 \qquad (IV)$$

in which
X has the abovementioned meaning,
$R^4$ represents an alkyl radical (1 to 10 C atoms) and
$R^5$ represents a protective group for an OH or SH group, in inert organic solvents, at temperatures between 0° C. and 120° C., and then eliminating the protective group $R^5$, when lactonization occurs, or (B) reacting benzylidene compounds of the general formula (V)

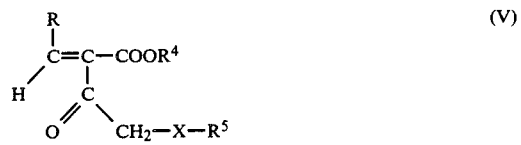

in which X, R, $R^4$ and $R^5$ have the abovementioned meanings, with compounds of the general formula (III), in which $R^1$ and $R^2$ have the abovementioned meanings, and then removing the protective group $R^5$, when lactonization occurs, or (C) reacting benzylidene compounds of the general formula (VI)

in which R and X have the abovementioned meaning, with compounds of the general formula (III), in which $R^1$ and $R^2$ have the abovementioned meaning, in analogy to (A)

The compounds of the general formula (I) in which $R^1$ represents OH can be prepared by reacting compounds of the general formula (I), in which $R^1$ is not OH and which have been prepared by process variants A, B or C, with aqueous acids in the presence of inert organic solvents.

The reaction steps in the process according to the invention for the preparation of (I) ($R^1$=OH) can be carried out both as a one-pot reaction without isolation of the intermediates produced during it, or in separate reaction steps with isolation of the intermediates (I) ($R^1$=OH).

Process C is preferred when it is intended to obtain compounds of the structure (I) with $R^1 \neq OH$.

Processes A and B followed by exchange of the amino group by the OH group are preferably carried out as one-pot reactions, especially for the synthesis of (I) with $R^1$=OH.

The compounds of the general formula (III) are known or can be prepared by known processes (J. Am. Chem. Soc. 67, 1017 (1945)).

The compounds of the general formula (IV) are known or can be prepared by known processes (Tetrahedron 34, 1543 (1978)).

The compounds of the general formula (V) are known or can be prepared by known processes (for example J. Am. Chem. Soc. 66, 1933 (1944)).

The compounds of the general formula (VI) are known or can be prepared by known processes (J. Heterocycl. Chem. 20 (1983), 787, J. org. Chem. 43, (1978), 1541 or Z. Chem. 10, 341 (1970).

The preferred inert organic solvents used in carrying out process variant A are alcohols, such as, for example, ethanol or tert.-butanol, and carboxylic acids, such as, for example, acetic acid or propionic acid.

The selected reaction temperature is preferably a temperature between 20° and 100° C., particularly the boiling point of the solvent used.

The elimination of the protective group $R^5$ is preferably carried out with suitable eliminating agents, such as, for example, the customary organic or inorganic acids or organic and inorganic bases.

Preferred protective groups ($R^5$) which may be mentioned are: acyl radicals, such as, for example, acetyl; trialkylsilyl radicals, or the tert.-butyl radical.

Unless expressly indicated otherwise, the reaction conditions and reaction media which have been mentioned as preferred also apply to process variants B and C.

The conversion, by a subsequent reaction step, of the compound of the general formula (I) in which $R^1$ does not denote hydroxyl into those compounds in which $R^1$ denotes hydroxyl is carried out in a customary manner, preferably by reaction with inorganic acids, such as hydrochloric acid or sulphuric acid, at the same time in the presence of inert organic solvents, such as alcohols, for example ethanol, propanol or tert.-butanol; ethers, such as diethyl ether, tetrahydrofuran or dioxane. This subsequent introduction of the hydroxyl group is preferably carried out at temperatures between 10° and 150° C., preferably at 20° to 100° C., in particular at the boiling point of the solvent.

The compounds according to the invention exhibit a valuable spectrum of pharmacological effects which could not have been foreseen. They can be used as cardiotonics to improve the myocardial contractility. Furthermore, due to the fact that they increase the inflow of $Ca^{++}$ into the cell, they can be used as antihypotensives, to reduce blood sugar, to reduce swelling of mucous membranes and to affect the salt and/or fluid balance.

The compounds according to the invention can be converted in a known manner into the customary formulations, such as tablets, capsules, coated tablets, pills, granules, aerosols, syrups, emulsions, suspensions and solutions, using inert, non-toxic, pharmaceutically suitable vehicles or solvents. The therapeutically active compounds should in each case be present in a concentration of about 0.5 to 90% by weight of the total mixture, that is to say in amounts which suffice to achieve the dosage range indicated.

The formulations are prepared, for example, by extending the active compounds with solvents and/or vehicles, optionally with the use of emulsifiers and/or dispersing agents, and, for example when using water as a diluent, organic solvents can optionally be used as auxiliary solvents.

Examples of auxiliaries which may be mentioned are: water, non-toxic organic solvents, such as paraffins (for example petroleum fractions), vegetable oils (groundnut oil/sesame oil), alcohols (for example ethyl alcohol and glycerol) and glycols (for example propylene glycol and polyethylene glycol), solid vehicles, such as, for example, natural rock powders (for example kaolins, aluminas, talc and chalk), synthetic rock powders (for example highly disperse silica and silicates) and sugars (for example sucrose, lactose and glucose), emulsifiers (for example polyoxyethylene fatty acid esters, polyoxyethylene fatty alcohol ethers, alkylsulphonates and arylsulphonates), dispersing agents (for example lignin, sulphite waste liquors, methylcellulose, starch and polyvinylpyrrolidone) and lubricants (for example magnesium stearate, talc, stearic acid and sodium lauryl sulphate).

Administration is effected in the customary manner, preferably orally or parenterally, in particular perlingually or intravenously. In the case of oral administration, the tablets can, of course, also contain, in addition to the vehicles mentioned, additives such as sodium citrate, calcium carbonate and dicalcium phosphate, together with various additional substances, such as starch, preferably potato starch, gelatine and the like. Furthermore, lubricants such as magnesium stearate, sodium lauryl sulphate and talc can also be used when making tablets. In the case of aqueous suspensions and/or elixirs which are intended for oral use, the active compounds can be mixed with various flavor-improving agents or colorants in addition to the abovementioned auxiliaries.

In the case of parenteral administration, solutions of the active compounds, employing suitable liquid vehicles, can be used.

In general, it has proved advantageous, in the case of intravenous administration, to administer amounts of about 0.0001 to 1 mg/kg, preferably about 0.001 to 0.5 mg/kg, body weight to achieve effective results, and in the case of oral administration, the dosage is about 0.01 to 20 mg/kg, preferably 0.1 to 10 mg/kg, body weight.

Nevertheless, it can at times be necessary to deviate from the amounts mentioned, and in particular to do so as a function of the body weight of the experimental animal or of the nature of the administration method, but also because of the species of animal and its individual behavior towards the medicament, and the nature of the formulation of the medicament and the time or interval over which the administration takes place. Thus it can suffice in some cases to manage with less than the abovementioned minimum amount, whilst in other cases the upper limit mentioned must be exceeded. Where relatively large amounts are administered, it can be advisable to divide these into several individual administrations over the course of the day. The same dosage range is envisaged for administration in human medicine. In this connection, the above statements similarly apply.

The compound of Example 3 shows an increase of contraction of the atrium of more than 50% at a concentration of $10^{-5}$ g/ml according to the following test method with isolated left guinea pig atrium.

Male or female adult guinea-pigs were sacrified by a fatal blow to the head. The hearts were removed, and the left atria separated from the ventricles. The atria were then suspended in 100 ml organ baths containing Krebs-Henseleit solution with 1.8 mmol/l Ca and 11 mmol/l glucose, maintained at 30° C. and oxygenated with 95% $O_2$+5% $CO_2$. Drugs were dissolved in 0.9% NaCl, when necessary in dimethylsulfoxide to 1 mg/ml, and serial dilutions were made with 0.9% NaCl. 1 ml of each drug dilution was injected into the organ bath (100 ml) yielding final drug concentrations from $10^{-8}$ to $10^{-5}$ g/ml. The atria were maintained at 1.0 g initial tension and stimulated with square wave pulses (1 Hz, 2 msec, 22 Volt). Contractions were measured isometrically with Statham UC2 strain gauges connected to a data acquisition system 12 min after the addition of the respective drug dose over a period of one min. The mean value of 60 contractions was calculated and expressed as percentage of the preceeding control period. Washings were performed with the aid of magnetic valves and a timer automatically each 14 min. After each drug addition three control periods without drug were run.

PREPARATION EXAMPLES

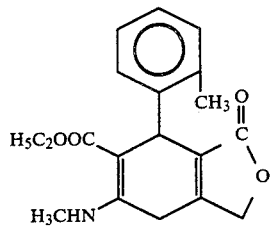

(1)

Ethyl 7-(2-methylphenyl)-5-methylamino-1-oxo-1,3,4,7-tetrahydrobenzo[c]furan-6-carboxylate (Process C)

20 mmol of 3-(2-methylbenzylidene)furan-2,4(3H,5H)-dione in 50 ml of ethanol and 20 mmol of ethyl 2-methylaminocrotonate were boiled under reflux overnight, and the mixture was concentrated and chromatographed on silica gel using toluene/ethyl acetate.

Melting point: 175°–181° C.

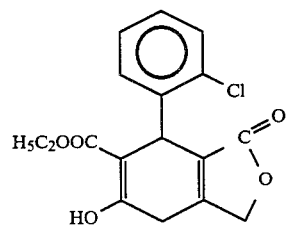

(2)

Ethyl 7-(2-chlorophenyl)-5-hydroxy-1-oxo-1,3,4,7-tetrahydrobenzo[c]furan-6-carboxylate (Process B)

20 mmol of ethyl 4-acetoxy-2-(2-chlorobenzylidene)-3-oxobutanecarboxylate together with 20 mmol of ethyl 3-butylaminocrotonate were boiled under reflux overnight, then 50 ml of concentrated HCl and 10 ml of water were added, and the mixture was boiled for a further hour. After cooling, the product is filtered off with suction.

Melting point: 181°–183° C.

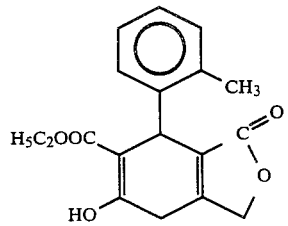

(3)

Ethyl 5-hydroxy-7-(2-methylphenyl)-1-oxo-1,3,4,7-tetrahydrobenzo[c]furan-6-carboxylate (a) Process A without isolation of the intermediate compound 50 mmol of 2-methylbenzaldehyde, 50 mmol of ethyl 3-butylaminocrotonate and 50 mmol of ethyl 4-acetoxy-3-oxobutanecarboxylate together with 100 ml of ethanol were boiled under reflux overnight, then 10 ml of concentrated HCl and 20 ml of water were added, and the mixture was boiled for a further hour. The product is recrystallized from ethanol.

Melting point: 145°–150° C.

(b) Preparation via the intermediate compound from Example 1

10 mmol of ethyl 7-(2-methylphenyl)-5-methylamino-1-oxo-1,3,4,7-tetrahydrobenzo[c]furan-6-carboxylate are dissolved in 50 mmol of THF, 3 ml of concentrated HCl and 5 ml of water are added, and the mixture is boiled for 1 hour and then concentrated. The substance is identical to that from Example 3(a).

The following were prepared in analogy to Example 3a:

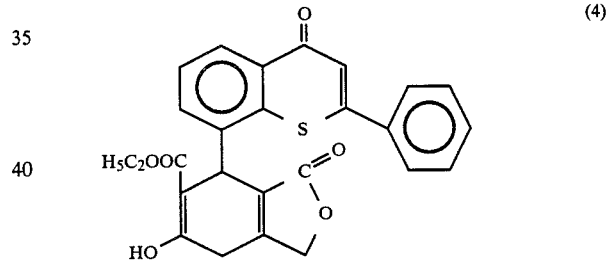

(4)

Ethyl 5-hydroxy-7-(4-oxo-2-phenyl-4H-thiochromen-8-yl)-1-oxo-1,3,4,7-tetrahydrobenzo[c]furan-6-carboxylate Melting point: 223°–226° C.

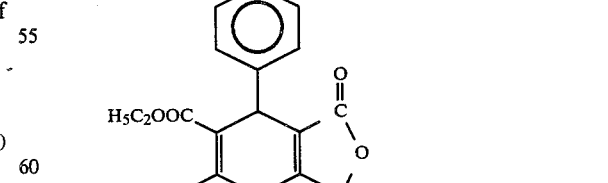

(5)

Ethyl 5-hydroxy-1-oxo-7-phenyl-1,3,4,7-tetrahydrobenzo[c]furan-6-carboxylate

Melting point: 153°–155° C.

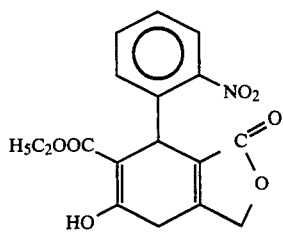

Ethyl
5-hydroxy-7-(2-nitrophenyl)-1-oxo-1,3,4,7-tetrahydrobenzo[c]furan-6-carboxylate Melting point: 183°–186° C.

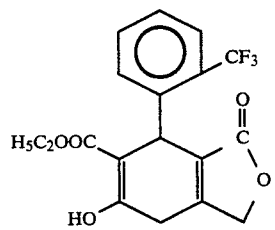

Ethyl
5-hydroxy-1-oxo-7-(2-trifluoromethylphenyl)-1,3,4,7-tetrahydrobenzo[c]furan-6-carboxylate Melting point: 150° C.

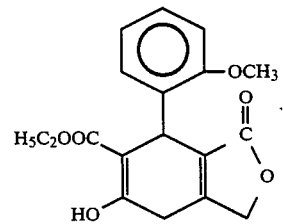

Ethyl
5-hydroxy-7-(2-methoxyphenyl)-1-oxo-1,3,4,7-tetrahydrobenzo[c]furan-6-carboxylate Melting point 169°–171° C.

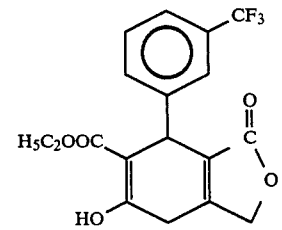

Ethyl
5-hydroxy-1-oxo-7-(3-trifluoromethylphenyl)-1,3,4,7-tetrahydrobenzo[c]furan-6-carboxylate Melting point: 149°–150° C.

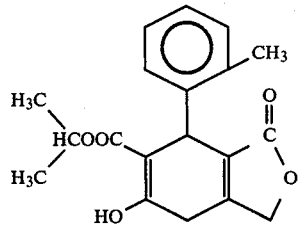

Isopropyl
5-hydroxy-7-(2-methylphenyl)-1-oxo-1,3,4,7-tetrahydrobenzo[c]furan-6-carboxylate Melting point: 155°–157° C.

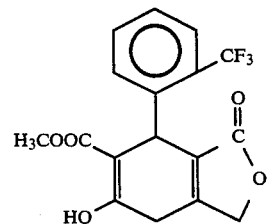

Methyl
5-hydroxy-1-oxo-7-(2-trifluoromethylphenyl)-1,3,4,7-tetrahydrobenzo[c]furan-6-carboxylate Melting point: 156°–159° C.

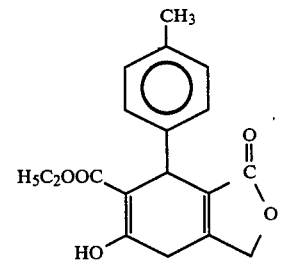

Ethyl
5-hydroxy-7-(4-methylphenyl)-1-oxo-1,3,4,7-tetrahydrobenzo[c]furan-6-carboxylate Melting point: 142°–148° C.

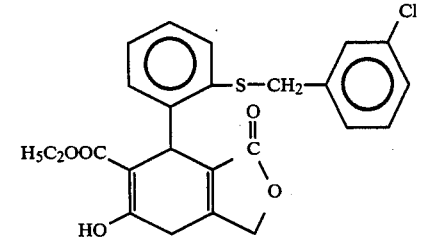

Ethyl
7-(2-[3-chlorobenzylthio]phenyl)-5-hydroxy-1-oxo-1,3,4,7-tetrahydrobenzo[c]furan-6-carboxylate Melting point: 155°–160° C.

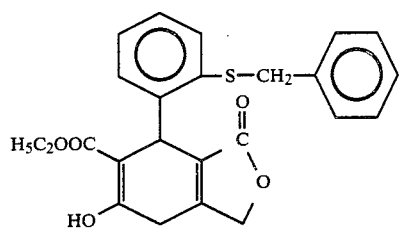

Ethyl
7-(2-benzylthiophenyl)-5-hydroxy-1-oxo-1,3,4,7-tetrahydrobenzo[c]furan-6-carboxylate Melting point: 144°–147° C.

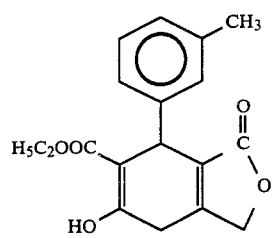

Ethyl
5-hydroxy-7-(3-methylphenyl)-1-oxo-1,3,4,7-tetrahydrobenzo[c]furan-6-carboxylate Melting point: 163°–166° C.

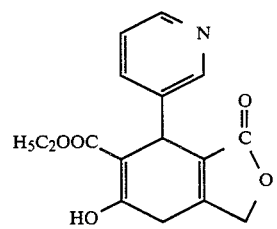

Ethyl
5-hydroxy-1-oxo-7-(3-pyridyl)-1,3,4,7-tetrahydrobenzo[c]furan-6-carboxylate Melting point: 172°–175° C.

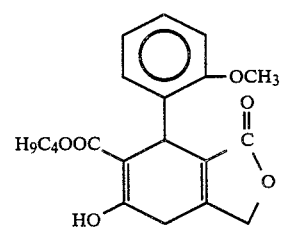

Butyl
5-hydroxy-1-oxo-7-(2-methoxyphenyl)-1,3,4,7-tetrahydrobenzo[c]furan-6-carboxylate Melting point: 66°–69° C.

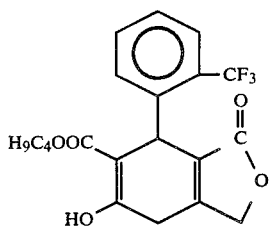

Butyl
5-hydroxy-1-oxo-7-(2-trifluoromethylphenyl)-1,3,4,7-tetrahydrobenzo[c]furan-6-carboxylate Melting point: 122°–127° C.

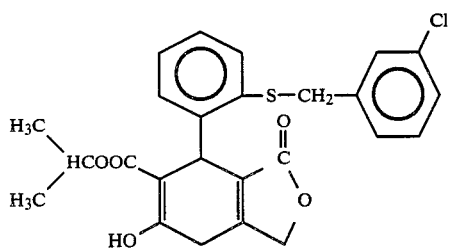

Isopropyl
7-(2-[3-chlorobenzylthio]phenyl)-5-hydroxy-1-oxo-1,3,4,7-tetrahydrobenzo[c]furan-6-carboxylate Melting point: 111°–115° C.

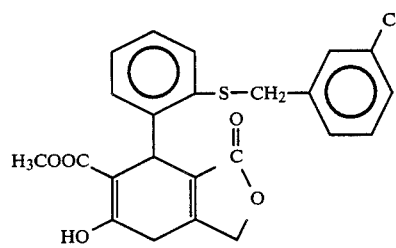

Methyl
7-(2-[3-chlorobenzylthio]phenyl)-5-hydroxy-1-oxo-1,3,4,7-tetrahydrobenzo[c]furan-6-carboxylate Melting point: 168°–171° C.

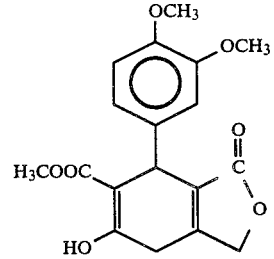

Methyl
7-(3,4-dimethoxyphenyl)-5-hydroxy-1-oxo-1,3,4,7-tetrahydrobenzo[c]furan-6-carboxylate Melting point: 158°–160° C.

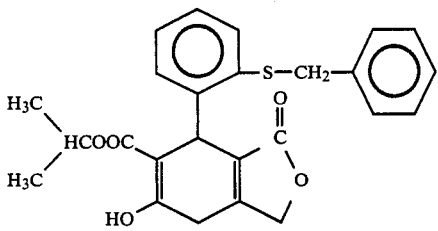

isopropyl
7-(2-benzylthiophenyl)-5-hydroxy-1-oxo-1,3,4,7-tetrahydrobenzo[c]furan-6-carboxylate Melting point: 149°–154° C.

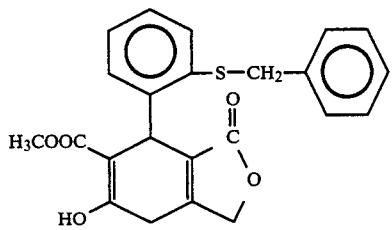

Methyl
7-(2-benzylthiophenyl)-5-hydroxy-1-oxo-1,3,4,7-tetrahydrobenzo[c]furan-6-carboxylate Melting point: 149°–154° C.

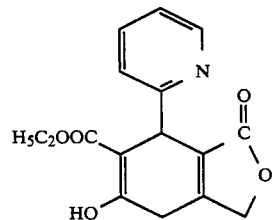

Ethyl
5-hydroxy-1-oxo-7-(2-pyridyl)-1,3,4,7-tetrahydrobenzo[c]furan-6-carboxylate Melting point: 133°–135° C.

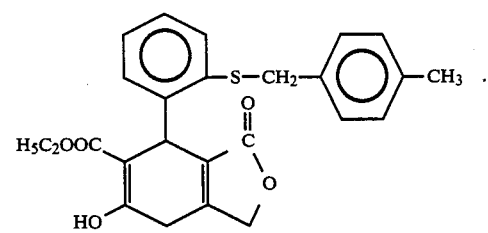

Ethyl
5-hydroxy-7-(2-[4-methylbenzylthio]-phenyl)-1,3,4,7-tetrahydrobenzo[c]furan-6-carboxylate Melting point: 130°–135° C.

It is understood that the specification and examples are illustrative but not limitative of the present invention and that other embodiments within the spirit and scope of the invention will suggest themselves to those skilled in the art.

We claim:

1. A furanone of the formula

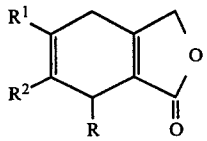

in which

R is an unsubstituted phenyl, naphthyl or pyridyl radical, or a phenyl, naphthyl or pyridyl radical which contains 1 to 3 identical or different substituents from the group consisting of alkyl (1 to 20 carbon atoms, alkenyl (2 to 20 carbon atoms, alkinyl (2 to 20 C atoms), alkoxy (1 to 16 C atoms), fluorine, chlorine, bromine, iodine, trifluoromethyl, monofluoroalkoxy (1 to 8 C atoms), polyfluoroalkoxy (1 to 8 C atoms), hydroxyl, amino, monoalkylamino (1 to 8 C atoms), dialkylamino (1 to 8 C atoms), nitro, cyano, azido, carboxyl, ($C_1$–$C_{10}$)alkoxy carbonyl, carboxamido, sulphonamido, $SO_m$-alkyl (m=0 to 2, 1 to 20 C atoms), unsubstituted phenyl, unsubstituted benzyl, unsubstituted benzyloxy or unsubstituted benzylthio, or phenyl, benzyl, benzyloxy or benzylthio which contain 1 to 3 radicals from the group consisting of alkyl (1 to 5 C atoms), alkoxy (1 to 5 C atoms), alkylthio (1 to 5 C atoms), fluorine, chlorine, bromine, iodine, cyano, nitro, azido, hydroxyl, trifluoromethyl, amino, alkylamino (1 to 6 C atoms) or dialkylamino (1 to 6 C atoms), $R^1$ represents hydroxyl, NH-alkyl (1 to 15 C atoms) or N(alkyl)$_2$ (each 1 to 15 C atoms), and $R^2$ represents the radical —$COR^3$ or $COOR^3$, and where $R^3$ represents an unsubstituted straight-chain, branched or cyclic alkyl or alkenyl radical having up to 12 C atoms or a straight-chain, branched or cyclic alkyl or alkenyl radical having up to 12 C atoms which is substituted by alkoxy or alkylthio having 1 to 4 C atoms in each case, fluorine, chlorine, cyano, hydroxyl, amino, alkylamino or dialkylamino having 1 to 4 C atoms in each alkyl group, nitro, phenyl or pyridyl, or a physiologically acceptable salt thereof.

2. A compound or salt according to claim 1,
in which

R represents an unsubstituted phenyl, naphthyl or pyridyl radical, or a phenyl, naphthyl or pyridyl radical which contains 1 to 3 identical or different substituents from the group consisting of alkyl (1 to 20 carbon atoms), alkenyl (2 to 16 carbon atoms), alkinyl (2 to 16 C atoms), alkoxy (1 to 16 C atoms), fluorine, chlorine, bromine, iodine, trifluoromethyl, monofluoroalkoxy (1 to 8 C atoms), polyfluoroalkoxy (1 to 8 C atoms), hydroxyl, amino, monoalkylamino (1 to 8 C atoms), dialkylamino (1 to 8 C atoms), nitro, cyano, azido, carboxyl ($C_1$–$C_8$)alkoxy carbonyl, $SO_m$-alkyl (m=0 to 2, 1 to 14 C atoms), unsubstituted phenyl, unsubstituted benzyl, unsubstituted benzyloxy or unsubstituted benzylthio, or phenyl, benzyl, benzyloxy or benzylthio which contains 1 to 3 radicals from the group consisting of alkyl (1 to 3 C atoms), alkoxy (1 to 3 C atoms), alkylthio (1 to 3 C atoms), fluorine, chlorine, bromine, iodine, cyano, nitro, hydroxyl, trifluoromethyl, amino, alkylamino (1 to 3 C atoms) or dialkylamino (1 to 3 C atoms), $R^1$ represents hydroxyl, NH-alkyl (1 to 10 C atoms) or N(alkyl)$_2$ (each 1 to 10 C atoms), and $R^2$ represents the radical COOR$^3$.

3. A compound or salt according to claim 1, in which

R represents unsubstituted phenyl, naphthyl or pyridyl, or phenyl, naphthyl or pyridyl substituted by 1 to 3 identical or different substituents from the group consisting of alkyl having 1 to 4 carbon atoms, fluorine, chlorine, nitro, trifluoromethyl, alkoxy having 1 to 4 carbon atoms, hydroxyl, amino, dialkylamino having 1 to 4 C atoms in each case, cyano, carboxyl, alkoxycarbonyl, unsubstituted phenyl, unsubstituted benzyl, unsubstituted benzyloxy or unsubstituted benzylthio, or phenyl, benzyl, benzyloxy or benzylthio bearing 1 or 2 identical or different substituents from the group consisting of alkyl, alkoxy, alkylthio having 1 to 4 C atoms in each case, fluorine, chlorine, cyano, hydroxyl, trifluoromethyl or nitro, each case, fluorine, chlorine, cyano, hydroxyl, trifluoromethyl or nitro, $R^1$ represents hydroxyl, NH-alkyl having 1 to 4 C atoms or dialkylamino having 1 to 4 C atoms in each alkyl group, and $R^2$ represents the radical COOR$^3$.

4. A compound according to claim 1, wherein such compound is ethyl 7-(2-methylphenyl)-5-methylamino-1-oxo-1,3,4,7-tetrahydrobenzo[c]furan-6-carboxylate of the formula

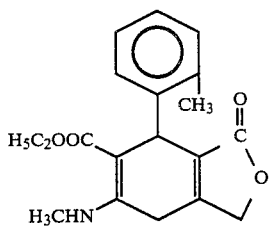

or a physiologically acceptable salt thereof.

5. A compound according to claim 1, wherein such compound is ethyl 7-(2-[3-chlorobenzylthio]phenyl)-5-hydroxy-1-oxo-1,3,4,7-tetrahydrobenzo[c]furan-6-carboxylate of the formula

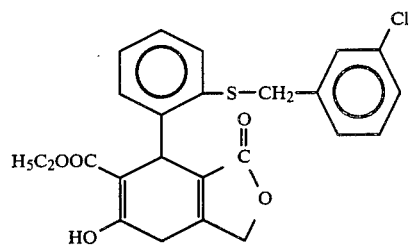

6. A compound according to claim 1, wherein such compound is ethyl 7-(2-benzylthiophenyl)-5-hydroxy-1-oxo-1,3,4,7-tetrahydrobenzo[c]furan-6-carboxylate of the formula

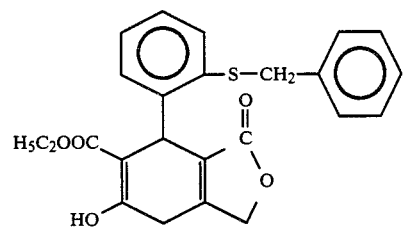

7. A compound according to claim 1, wherein such compound is ethyl 5-hydroxy-1-oxo-7-(2-pyridyl)-1,3,4,7-tetrahydrobenzo[c]furan-6-carboxylate of the formula

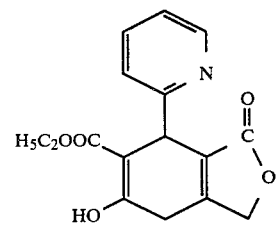

8. A composition for improving myocardial contractility comprising an effective amount of a compound or salt according to claim 1 and a diluent.

9. A unit dose of a composition according to claim 8 in the form of a tablet, capsule or ampule.

10. A method of improving the myocardial contractility of a patient in need thereof which comprises administering to such patient an amount effective therefor of a compound or salt according to claim 1.

11. The method according to claim 10, wherein such compound is ethyl 7-(2-methylphenyl)-5-methylamino-1-oxo-1,3,4,7-tetrahydrobenzo[c]furan-6-carboxylate or a physiologically acceptable salt thereof, ethyl 7-(2-[3-chlorobenzylthio]phenyl)-5-hydroxy-1-oxo-1,3,4,7-tetrahydrobenzo[c]furan-6-carboxylate, ethyl 7-(2-benzylthiophenyl)-5-hydroxy-1-oxo-1,3,4,7-tetrahydrobenzo[c]furan-6-carboxylate or ethyl 5-hydroxy-1-oxo-7-(2-pyridyl)-1,3,4,7-tetrahydrobenzo[c]furan-6-carboxylate.

* * * * *